United States Patent

Zinke et al.

[11] Patent Number: 5,804,622
[45] Date of Patent: Sep. 8, 1998

[54] MONOMERIC N-PIPERIDINYLMELAMINES AS STABILIZERS FOR CHLORINE-CONTAINING POLYMERS

[75] Inventors: Horst Zinke, Reichelsheim/Odw.; Wolfgang Wehner, Ober-Ramstadt; Karl Josef Kuhn, Lautertal, all of Germany; Valerio Borzatta, Bologna, Italy; Gerhard Rytz, Bern, Switzerland

[73] Assignee: Ciba Specialty Chemicals Corporation, Tarrytown, N.Y.

[21] Appl. No.: 819,224

[22] Filed: Mar. 17, 1997

[30] Foreign Application Priority Data

Mar. 22, 1996 [CH] Switzerland ................ 1996 0752/96

[51] Int. Cl.⁶ .................................................. C08K 5/3492
[52] U.S. Cl. .................... 524/100; 524/399; 524/432; 524/434; 524/437; 544/198; 252/400.24; 252/400.52; 252/401; 252/403
[58] Field of Search .................. 524/100, 399, 524/432, 434, 437; 544/198; 252/400.24, 400.52, 401, 403

[56] References Cited

U.S. PATENT DOCUMENTS

| | | | |
|---|---|---|---|
| 3,714,114 | 1/1973 | Stretanski | 524/100 |
| 4,929,652 | 5/1990 | Gugumus | 524/91 |
| 5,037,870 | 8/1991 | Gugumus | 524/102 |
| 5,194,470 | 3/1993 | Carette et al. | 524/178 |
| 5,244,949 | 9/1993 | Wirth et al. | 524/100 |
| 5,283,273 | 2/1994 | Sander et al. | 524/100 |
| 5,350,785 | 9/1994 | Sander et al. | 524/100 |

FOREIGN PATENT DOCUMENTS

| | | |
|---|---|---|
| 2026899 | 4/1991 | Canada . |
| 2031436 | 6/1991 | Canada . |
| 2037676 | 9/1991 | Canada . |
| 0290388 | 11/1988 | European Pat. Off. . |
| 0468923 | 1/1992 | European Pat. Off. . |
| 0690094 | 1/1996 | European Pat. Off. . |
| 2300192 | 10/1996 | United Kingdom . |

OTHER PUBLICATIONS

Chemical Abstract No. 117:2525249.

*Primary Examiner*—Kriellion S. Morgan
*Attorney, Agent, or Firm*—Luther A. R. Hall

[57] ABSTRACT

A stabilizer combination, principally for PVC, is described, comprising A at least one zinc carboxylate B at least one compound of the formula

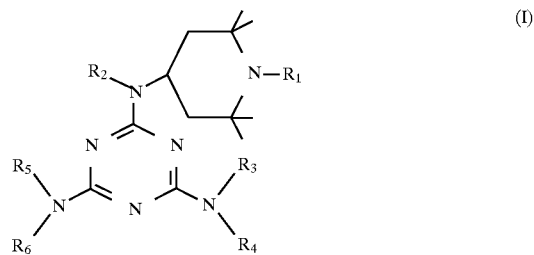

in which $R_1$ to $R_6$ are as defined in claim 1.

12 Claims, No Drawings

MONOMERIC N-PIPERIDINYLMELAMINES AS STABILIZERS FOR CHLORINE-CONTAINING POLYMERS

The invention relates to a stabilizer combination comprising an organozinc compound which contains a Zn—O or Zn—S bond, and at least one compound of the formula I below, which combination is suitable for stabilizing chlorine-containing polymers, especially PVC.

PVC can be stabilized by a range of additives. Compounds of lead, of barium and of cadmium are particularly suitable for this, but are nowadays controversial on ecological grounds (cf. "Taschenbuch der Kunststoffadditive", eds. R. Gachter and H. Muller, Carl Hanser Verlag, 3rd.edition, 1989, pages 303–311, and Kunststoff Handbuch PVC, volume 2/1, G. W. Becker, D. Braun, Carl Hanser Verlag 1985, pages 531–538). The search is therefore continuing for effective stabilizers and stabilizer combinations devoid of disadvantageous properties.

Sterically hindered amines have already been added to the PVC as light stabilizers. The thermal stability can also be favourably affected (cf. e.g. EP 366 271 and EP 488 951).

It has now been found that organozinc compounds, for example zinc carboxylates, are used advantageously with compounds of the formula I,

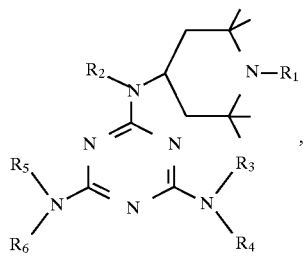

in which $R_1$ is H, $C_{1-8}$alkyl-, $C_{3-8}$alkenyl-, $C_{5-8}$cycloalkyl- or $C_{7-9}$phenylalkyl-;

$R_2$ is H, $C_{1-8}$alkyl-, $C_{3-8}$alkenyl-, $C_{5-8}$cycloalkyl-, HO—$C_2H_4$—, HO—$C_3H_6$—,$(C_{1-4}$alkylk$)_2$N—$(CH_2)_k$—,

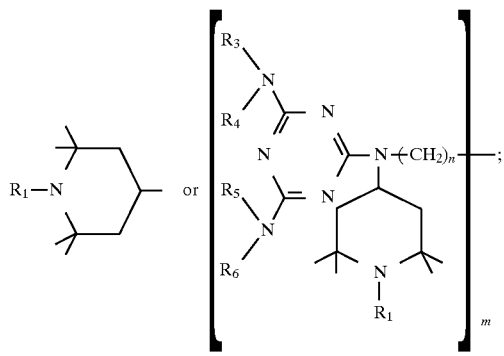

$R_3$, $R_4$, $R_5$, and $R_6$ independently of one another are H, $C_{1-8}$alkyl-, $C_{5-8}$cycloalkyl-, $C_{7-9}$phenylalkyl-, $C_{3-8}$alkenyl-, HO—$C_2H_4$—, HO—$C_3H_6$—, $(C_{1-4}$alkyl$)_2$N—$(CH_2)_k$—, phenyl or phenyl substituted by HO—, $H_2$N—, $C_{1-4}$alkyl- or $C_{1-4}$alkoxy, or $R_3$, $R_4$, $R_5$, and $R_6$ are

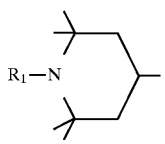

and $R_3$ and $R_4$ and/or $R_5$ and $R_6$ can alternatively be attached to one
another via methylene groups, which are adjacent or separated by O, S or $C_{1-4}$alkyl-N atoms; and n is 2 to 12;

k is 2 to 6; and m is 0 or 1.

$C_{1-4}$alkyl is methyl, ethyl, n-propyl, iso-propyl, n-, i-, sec- or t-butyl.

$C_{5-8}$cycloalkyl is, for example, cyclopentyl, cyclohexyl, cycloheptyl or cyclooctyl. Cyclopentyl and especially cyclohexyl are preferred.

$C_{3-8}$alkenyl is branched or unbranched alkenyl, for example allyl, crotonyl, 2-methylallyl or hexenyl.

$C_{1-4}$alkoxy is, for example, methoxy, ethoxy, propoxy, isopropoxy, butoxy or isobutoxy.

$C_{7-9}$phenylalkyl is, for example, benzyl, 1- or 2-phenylethyl, 3-phenylpropyl, α,α-dimethylbenzyl or 2-phenylisopropyl, preferably benzyl.

Preferred compounds of the formula I are those in which $R_1$ is H or $C_{1-8}$alkyl-;

$R_2$ is H, $C_{1-8}$alkyl-, HO—$C_2H_4$—, HO—$C_3H_6$—, $(C_{1-4}$alkyl$)_2$N—$(CH_2)_k$—,

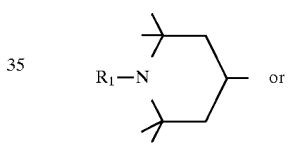

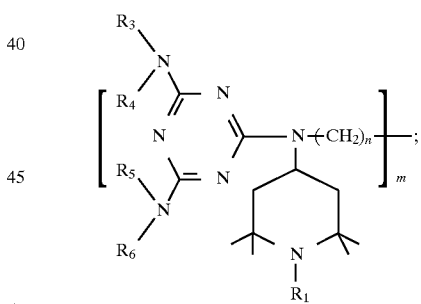

$R_3$, $R_4$, $R_5$, and $R_6$ are H, $C_{1-8}$alkyl-, HO—$C_2H_4$—, HO—$C_3H_6$—, $(C_{1-4}$alkyl$)_2$N—$(CH_2)_k$—,

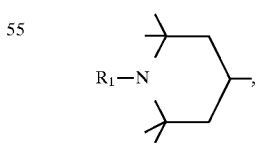

or $NR_3R_4$ and/or $NR_5R_6$ are groups of the formulae

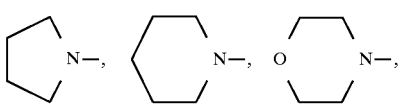

-continued

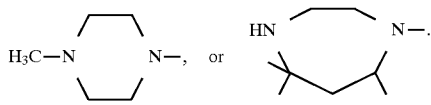

Particularly preferred compounds of the formula I are those in which $R_1$ is H or $C_{1-4}$alkyl-;
$R_2$ is H, $C_{1-4}$alkyl-, $(C_{1-4}$alkyl$)_2$N—$(CH_2)_k$—,

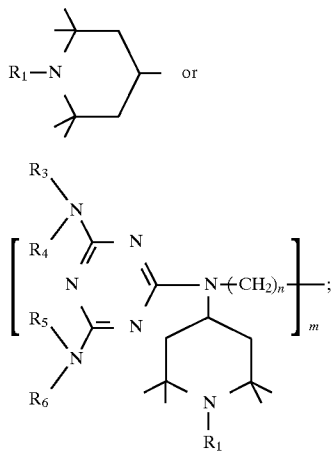

$R_3$, $R_4$, $R_5$, and $R_6$ are H, $C_{1-4}$alkyl-, $(C_{1-4}$alkyl$)_2$N—$(CH_2)_k$—,

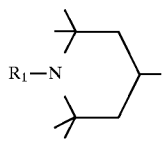

or $NR_3R_a$ and/or $NR_5R_6$ are groups of the formulae

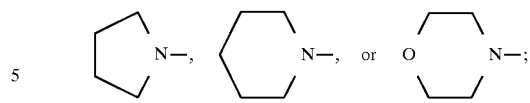

and
n is 2 to 6;
k is 2 or 3; and
m is 0 or 1.

Very particularly preferred compounds of the formula I are those in which
$R_3$, $R_4$, $R_5$ and $R_6$ independently of one another are H,

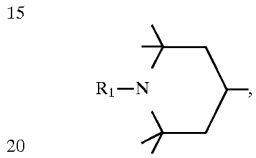

or $NR_3R_4$ and/or $NR_5R_6$ are groups of the formulae

Some of the compounds of the formula I are novel. The invention therefore also relates to compounds of the formula I, as described at the start, wherein at least one of the radicals $R_2$–$R_6$ is $(C_{1-4}$alkyl$)_2$N—$(CH_2)_k$— and the other radicals are as defined at the beginning; and to compounds of the formula I wherein $R_3$–$R_6$ are hydrogen and the remaining radicals are as defined at the beginning.

The content of compounds of the formula I in the chlorine-containing polymer is from 0.005 to 5, preferably from 0.01 to 2 and, in particular from 0.01 to 1%.

Examples of N-piperidinylmelamines of the formula I are compounds of the following structure:

TABLE 1

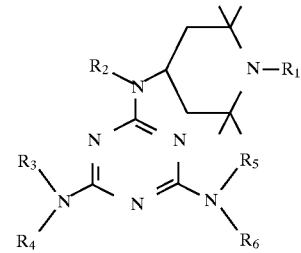

| No. | $R_2$—N... N—$R_1$ | $R_3$\N—/$R_4$ | $R_5$\N—/$R_6$ |
|---|---|---|---|
| 1 | PMP—NH— | H$_2$N— | H$_2$N— |
| 2 | TMP—NH— | TMP—NH— | H$_2$N— |
| 3 | TMP—NH— | Me$_2$N— | Me$_2$N— |
| 4 | TMP—NH— | TMP—NH— | TMP—NBu— |
| 5 | TMP—NH— | TMP—NH— | (HO—CH$_2$CH$_2$—)$_2$N— |
| 6 | TMP—NH— | HO—CH$_2$CH$_2$—NH— | TMP—NBu— |
| 7 | (TMP)$_2$N— | H$_2$N— | H$_2$N— |

TABLE 1-continued

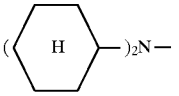

| No. | R₂—N(R-)—... (piperidine col) | R₃—N(R₄)— | R₅—N(R₆)— |
|---|---|---|---|
| 8 | TMP—NH— | (C₆H₁₁(H))₂N— | (C₆H₁₁(H))₂N— |
| 9 | (TMP)₂N— | (TMP)₂N— | (TMP)₂N— |
| 10 | PMP—NH— | PMP—NH— | PMP—NH— |
| 11 | (i-Pr)₂N—C₂H₄—N(TMP)— | Pr₂N— | Pr₂N— |
| 12 | (i-Pr)₂N—C₂H₄—N(TMP)— | TMP—NH | TMP—NH |
| 13 | TMP—NH | Et₂N— | TMP—NH— |
| 14 | TMP—NH | (HOCH₂)₃C—NH— | TMP—NH— |
| 15 | TMP—NH— | morpholin-N— | Et₂N—C₂H₄—NH— |
| 16 | TMP₂N— | TMP—NH— | Et₂N—C₂H₄—NH— |
| 17 | TMP—NH— | TMP—NH | C₆H₅CH₂NH— |
| 18 | TMP—NH— | 2-HO-C₆H₄-NH— | TMP—NH— |
| 19 | TMP—NH— | 2-MeO-C₆H₄-NH— | 2-MeO-C₆H₄-NH— |
| 20 | TMP—NH— | Et₂N—C₂H₄—NH— | 4-EtO-C₆H₄-NH— |
| 21 | TMP—N(n-Bu)— | Et₂N— | Et₂N— |
| 22 | TMP—N(Et)— | (n-Bu)₂N— | TMP—N(Et)- |
| 23 | TMP—NH— | 4-methylpiperazin-1-yl— | TMP—NH— |
| 24 | TMP—NH— | (hexahydrodiazepine) HN...N— | TMP—NH— |

TABLE 1-continued

[General structure: triazine core with three N(R)(R') branches — R2/R1 on top amine, R3/R4 and R5/R6 on the other two amines, where one substituent connects via a 2,2,6,6-tetramethylpiperidin-4-yl group]

| No. | $R_2\text{−N(R_1)}$ — (piperidinyl) | $R_3\text{−N−R_4}$ | $R_5\text{−N−R_6}$ |
|---|---|---|---|
| 25 | CH$_2$=CH−CH$_2$−N< (TMP)−NH− | piperidino (N−) | piperidino (N−) |
| 26 | C$_6$H$_5$−CH$_2$−N< (TMP)−NH− | pyrrolidino (N−) | pyrrolidino (N−) |
| 27 | CH$_2$=CH−CH$_2$−N< (TMP)−NH− | TMP−NH− | TMP−NH− |
| 28 | TMP−NH− | (HO−C$_2$H$_4$)$_2$N− | (HO−C$_2$H$_4$)$_2$N− |
| 29 | Et$_2$N−(CH$_2$)$_3$−N−TMP | TMP−NH− | TMP−NH− |
| 30 | i-C$_3$H$_7$N−TMP | PMP−NH− | PMP−NH− |
| 31 | HO−CH$_2$CH$_2$−N−TMP | pyrrolidino (N−) | pyrrolidino (N−) |
| 32 | [melamine-type: H$_2$N–triazine(NH$_2$)−N((CH$_2$)$_6$−N−TMP)− attached to TMP (NH)] | H$_2$N− | H$_2$N− |
| 33 | cyclohexyl−N(H)−PMP | TMP−NH− | TMP−NH− |
| 34 | C$_4$H$_9$−N−TMP | morpholino (O⌒N−) | morpholino (O⌒N−) |

TABLE 1-continued

| No. | $R_2-N(-)-N-R_1$ (with piperidine) | $R_3-N(-R_4)$ | $R_5-N(-R_6)$ |
|---|---|---|---|
| 35 | C₈H₁₇—N(—)—TMP | TMP—NH— | TMP—NH— |
| 36 | (structure with two pyrrolidines on triazine, linked via N—(CH₂)₆—N—TMP to piperidine-NH) | pyrrolidine-N— | pyrrolidine-N— |
| 37 | HO—C₃H₆—N(—)—PMP | TMP—NH— | TMP—NH— |
| 38 | (i-Prop)₂N—C₂H₄—N(—)—TMP | (i-Pr)₂N—C₂H₄—NH— | (i-Pr)₂N—C₂H₄—NH— |
| 39 | (structure with two Et₂N groups on triazine, linked via N—(CH₂)₆—N—TMP to piperidine-NH) | Et₂N— | Et₂N— |
| 40 | (structure with two Bu₂N groups on triazine, linked via N—(CH₂)₃—N—TMP to piperidine-NH) | Bu₂N— | Bu₂N— |

TABLE 1-continued

| No. | 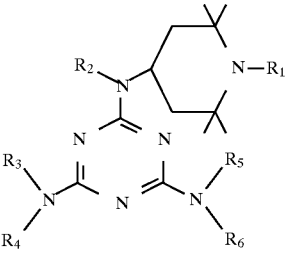 | 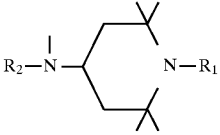 |  |
|---|---|---|---|
| 41 | TMP—NH <br>  | TMP—NH— | TMP—NH— |
| 42 | PMP—NH <br> 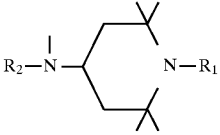 | PMP—NH— | $Et_2N-C_2H_4-NH-$ |
| 43 | $(TMP_2)N-$ | $(i-Pr)_2N-C_2H_4-NH-$ | $(i-Pr)_2N-C_2H_4-NH-$ |
| 44 | TMPNH— | $Et_2N-C_3H_6-NH-$ | $Et_2N-C_3H_6-NH-$ |
| 45 |  | TMP—N(Bu)— | TMP—N(Bu)— |

Key:

Key: TMP = 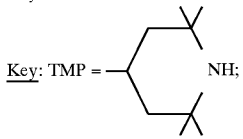

PMP = 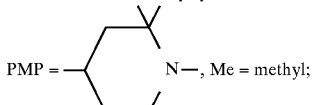, Me = methyl;

Et = ethyl; Pr = propyl; Bu = butyl.

ZINC COMPOUNDS

The organozinc compounds with a Zn—O bond comprise zinc enolates, zinc phenolates and/or zinc carboxylates. The latter are compounds from the series of the aliphatic saturated and unsaturated $C_1$–$C_{22}$ carboxylates, the aliphatic saturated or unsaturated $C_2$–$C_{22}$ carboxylates, which are substituted with at least one OH group or whose chain is interrupted by one or more O atoms (oxa acids), the cyclic and bicyclic carboxylates of 5–22 carbon atoms, the unsubstituted, mono- or poly-OH-substituted and/or $C_{1-16}$alkyl-substituted phenylcarboxylates, the phenyl-$C_{1-16}$alkylcarboxylates, or the unsubstituted or $C_{1-12}$alkyl-substituted phenolates, or of abietic acid. Examples of Zn—S compounds are Zn mercaptides, Zn mercaptocarboxylates and Zn mercaptocarboxylic esters.

Mention may be made by name, as examples, of the zinc salts of monovalent carboxylic acids, such as acetic acid, propionic acid, butyric acid, valeric acid, hexanoic acid, oenanthic acid, octanoic acid, neodecanoic acid, 2-ethylhexanoic acid, pelargonic acid, decanoic acid, undecanoic acid, dodecanoic acid, tridecanoic acid, myristylic acid, palmitic acid, lauric acid, isostearic acid, stearic acid, 12-hydroxystearic acid, 9,10-dihydroxystearic acid, oleic acid, ricinoleic acid, 3,6-dioxaheptanoic acid, 3,6,9-trioxadecanoic acid, behenic acid, benzoic acid, p-tert-butylbenzoic acid, dimethylhydroxybenzoic acid, 3,5-di-tert-butyl4-hydroxybenzoic acid, toluic acid, dimethylbenzoic acid, ethylbenzoic acid, n-propylbenzoic acid, salicylic acid, p-tert-octylsalicylic acid, and sorbic acid, cinnamic acid, mandelic acid, glycolic acid; zinc salts of divalent carboxylic acids and their monoesters, such as oxalic acid, malonic acid, succininic acid, glutaric acid, adipic acid, fumaric acid, pentane-1,5-dicarboxylic acid, hexane-1,6-dicarboxylic acid, heptane-1,7-dicarboxylic acid, octane-1,8-dicarboxylic acid, 3,6,9-trioxadecane-1,10-dicarboxylic acid, lactic acid, malonic acid, maleic acid, tartaric acid, malic acid, salicylic acid, polyglycoldicarboxylic acid (n=10–12), phthalic acid, isophthalic acid, terephthalic acid and hydroxyphthalic acid; and the di- or triesters of tri- or tetravalent carboxylic acids, such as hemimellitic acid, trimellitic acid, pyromellitic acid, citric acid and also so-called overbased zinc carboxylates, or zinc lauryl mercaptide, zinc thioglycolate, zinc thiosalicylate, zinc bis-i-octylthioglycolate, zinc mercaptopropionate, zinc thiolactate, zinc thiomalate, zinc-bis-octylmercaptopropionate, zinc bis-isooctylthiolactate and zinc bis-laurylthiomalate.

The zinc enolates preferably comprise enolates of acetylacetone, of benzoylacetone, and of dibenzoylmethane and enolates of acetoacetic and benzoylacetic esters, and of dehydroacetic acid. It is also possible to employ inorganic zinc compounds such as zinc oxide, zinc hydroxide, zinc carbonate, basic zinc carbonate or zinc sulfide.

Preference is given to neutral or basic zinc carboxylates of a carboxylic acid having 2 to 22 carbon atoms (zinc soaps), for example benzoates or alkanoates, preferably $C_8$alkanoates, stearate, oleate, laurate, palmitate, behenate, Versatate, hydroxystearates and -oleates, dihydroxystearates, p-tert-butylbenzoate, or (iso)octanoate. Particular preference is given to stearate, oleate, Versatate, benzoate, p-tert-butylbenzoate and 2-ethylhexanoate.

Also suitable in addition to the abovementioned zinc compounds are (in)organic aluminium compounds containing an Al—O bond. The aluminium compounds which can be used and are preferred include, preferably, aluminium enolates and aluminium carboxylates. Examples of carboxylate and enolate radicals can be found correspondingly under those listed above for zinc. Examples of inorganic Al compounds are aluminium hydroxide and aluminium phosphates.

The described metal soaps and/or their mixtures can be employed in amounts of, for example, from 0.001 to 10, expediently from 0.01 to 5, preferably from 0.01 to 3 parts by weight per 100 parts by weight of chlorine-containing polymer. They may also be present in the form of mixed salts (coprecipitates).

The novel stabilizer combination can be used together with further additives which are customary for the processing and stabilization of chlorine-containing polymers, examples being 1. Stabilizers:
   Epoxides and epoxidized fatty acid esters; phosphites; thiophosphites and thiophosphates;
   polyols; 1,3-dicarbonyl compounds; mercaptocarboxylic esters; dihydropyridines;
   antioxidants; light stabilizers and UV absorbers; alkali metal and alkaline earth metal compounds; perchlorate salts; zeolites; hydrotalcites; dawsonites;
2. Further common PVC additives, for example
   lubricants; plasticizers; impact modifiers; processing aids; blowing agents; fillers; antistats;
   biocides; antifogging agents; pigments and dyes; metal deactivators; flameproofing agents (cf. in this respect "Handbook of PVC Formulating", E. J. Wickson, John Wiley & Sons, New York 1993).

Examples of such additives are known to the skilled worker and can be found in the technical literature. Without limitation, mention may be made here of some of the known additives and processing aids:

Phosphites: Organic phosphites are known co-stabilizers for chlorine-containing polymers. Examples are trioctyl, tridecyl, tridodecyl, tritridecyl, tripentadecyl, trioleyl, tristearyl, triphenyl, tricresyl, trisnonylphenyl, tris-2,4-t-butylphenyl or tricyclohexyl phosphite. Further suitable phosphites are variously mixed aryl dialkyl and alkyl diaryl phosphites, such as phenyl dioctyl, phenyl didecyl, phenyl didodecyl, phenyl ditridecyl, phenylditetradecyl, phenyl dipentadecyl, octyl diphenyl, decyl diphenyl, undecyl diphenyl, dodecyldiphenyl, tridecyl diphenyl, tetradecyl diphenyl, pentadecyl diphenyl, oleyl diphenyl, stearyl diphenyl and dodecyl bis-2,4-di-t-butylphenyl phosphite.

Furthermore, phosphites of various diols and polyols can also be used advantageously; examples are tetraphenyidipropylene glycol diphosphite, polydipropylene glycol phenyl phosphite, tetramethylolcyclohexanol decyl diphosphite, tetramethylolcyclohexanol butoxyethoxyethyl diphosphite, tetramethylolcyclohexanol nonylphenyl diphosphite, bis-nonylphenyl ditrimethylolpropane diphosphite, bis-2-butoxyethyl di-trimethylolpropane diphosphite, trishydroxyethyl isocyanurate hexadecyl triphosphite, didecylpentaerythritol diphosphite, distearyl pentaerythritol diphosphite, bis-2,4-di-t-butylphenyl pentaerythritol diphosphite, and also mixtures of these phosphites and aryl/alkyl phosphite mixtures of the statistical composition $(H_{19}C_9—C_6H_4)O_{1.5}P$ $(OC_{12,13}H_{25,27})_{1.5}$ or $[C_8H_{17}—C_6H_6—O—]_2P[i—C_8H_{17}O]$ or $(H_{19}C_9—C_6H_4)O_{1.5}P(OC_{9,11}H_{19,23})_{1.5}$ The organic phosphites can be employed in an amount of, for example, from 0.01 to 10 parts by weight, expediently from 0.05 to 5 parts by weight and, in particular, from 0.1 to 3 parts by weight, based on 100 parts by weight of PVC.

Polyols: Examples of suitable compounds of this type are: pentaerythritol, dipentaerythritol, tripentaerythritol, bistrimethylolpropane, trimethylolethane, bistrimethylolethane, trimethylolpropane, sorbitol, maltitol, isomaltitol, lactitol, lycasine, mannitol, lactose, leucrose, tris(hydroxyethyl) isocyanurate, palatinite, tetramethylolcyclohexanol (TMCH), tetramethylolcyclopentanol, tetramethylolcyclopyranol, glycerol, diglycerol, polyglycerol, thiodiglycerol, or 1—O—α-D-glycopyranosyl-D-mannitol dihydrate, and also polyvinyl alcohol and cyclodextrins. Among these, TMCH and the disaccharide alcohols are preferred.

The polyols can be employed in an amount of, for example, from 0.01 to 20 parts by weight, expediently from 0.1 to 20 parts by weight, and, in particular, from 0.1 to 10 parts by weight, based on 100 parts by weight of PVC.

1,3-Dicarbonyl compounds: Examples of 1,3-dicarbonyl compounds are acetylacetone, butanoylacetone, heptanoylacetone, stearoylacetone, palmitoylacetone, lauroylacetone, 7-tert-nonylthioheptane-2,4-dione, benzoylacetone, dibenzoylmethane, lauroylbenzoylmethane, palmitoylbenzoylmethane, stearoylbenzoylmethane, isooctylbenzoylmethane, 5-hydroxycapronylbenzoylmethane, tribenzoylmethane, bis(4-methylbenzoyl)methane, benzoyl-p-chlorobenzoylmethane, bis(2-hydroxybenzoyl)methane, 4-methoxybenzoyl-benzoylmethane, bis(4-methoxybenzoyl)methane, 1-benzoyl-1-acetylnonane, benzoyl-acetylphenylmethane, stearoyl-4-methoxybenzoylmethane, bis(4-tert-butylbenzoyl)methane, benzoylformylmethane, benzoylphenylacetylmethane, bis(cyclohexanoyl)methane, di(pivaloyl)methane, acetoacetic methyl, ethyl, hexyl, octyl, dodecyl or octadecyl ester, benzoylacetic ethyl, butyl, 2-ethylhexyl, dodecyl or octadecyl ester, stearoylacetic ethyl, propyl, butyl, hexyl or octyl ester and dehydroacetic acid, and the zinc, alkali metal, alkaline earth metal or aluminium salts thereof.

The 1,3-dicarbonyl compounds can be employed in an amount of, for example, from 0.01 to 10 parts by weight, expediently from 0.01 to 3 parts by weight and, in particular, from 0.01 to 2 parts by weight, based on 100 parts by weight of PVC.

Thiophosphites and thiophosphates: Thiophosphites and thiophosphates are compounds of the general type $(RS)_3P$, $(RS)_3P=O$ and $(RS)_3P=S$, as described in the patent documents DE 2809492, EP 090770 and EP 573394. Examples are: trithiohexyl phosphite, trithiooctyl phosphite, trithiolauryl phosphite, trithiobenzyl phosphite, tris[carboxy-i-octyloxy]methyl trithiophosphate, S,S,S-tris[carbo-1-octyloxy]methyl trithiophosphate, S,S,S-tris[carbo-2-ethylhexyloxy]methyl trithiophosphate, S,S,S-tris-1-[carbohexyloxy]ethyl trithiophosphate, S,S,S-tris-1-[carbo-2-ethylhexyloxy]ethyl trithiophosphate, S,S,S-tris-2-[carbo-2-ethylhexyloxy]ethyl trithiophosphate.

The thiophosphites and thiophosphates can be present in the chlorine-containing polymer expediently in proportions of from 0.01 to 20%, preferably from 0.1 to 5% and, in particular, from 0.1 to 1%.

Mercaptocarboxylic esters: Examples of these compounds are esters of thioglycolic acid, thiomalic acid, mercaptopropionic acid, of mercaptobenzoic acids and of thiolactic acid, as are described in FR 2459816, EP 90748, FR 2552440 and EP 365483. The mercaptocarboxylic esters also embrace corresponding polyol esters and their partial esters.

They can be present in the chlorine-containing polymer expediently in proportions of from 0.01 to 10%, preferably from 0.1 to 5% and, in particular, from 0.1 to 1%.

Epoxides and epoxidized fatty acid esters: The novel stabilizer combination may additionally comprise at least one epoxidized fatty acid ester. Particularly suitable for this are esters of fatty acids from natural sources, such as soya oil or rapeseed oil.

The epoxy compounds are employed in amounts of, for example, upwards of 0.1 part per 100 parts by weight of composition, expediently from 0.1 to 30 parts, preferably from 0.5 up to 25 parts by weight. Further examples are epoxidized polybutadiene, epoxidized linseed oil, epoxidized fish oil, epoxidized tallow, methylbutyl or 2-ethylhexyl epoxystearate, tris-(epoxypropyl)isocyanurate, epoxidized castor oil, epoxidized sunflower oil, 3-phenoxy-1,2-epoxypropane, bisphenol A diglycidyl ether, vinylcyclohexene diepoxide, dicyclopentadiene diepoxide and 3,4-epoxycyclohexylmethyl 3,4-epoxycyclohexanecarboxylate. Also suitable as epoxides are derivatives of bisphenol A and of bisphenol F, as described, for example, in South African patent document ZA-2600194.

Dihydropyridines and polydihydropyridines: Suitable monomeric dihydropyridines are compounds as described, for example, in FR 2039496, EP 2007, EP 362012 and EP 24754. Preference is given to those of the formula

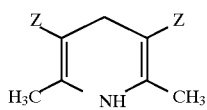

in which Z is $CO_2CH_3$, $CO_2C_2H_5$, $CO_2{}^nC_{12}H_{25}$ or $-CO_2C_2H_4-S-{}^nC_{12}H_{25}$.

Particularly suitable polydihydropyridines are compounds of the following formula

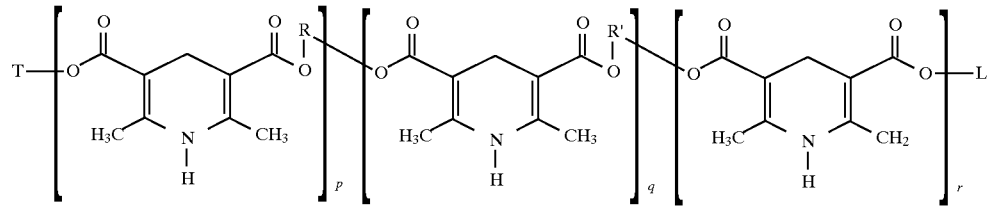

in which T is unsubstituted $C_{1-12}$alkyl,
L is as defined for T,
p and q are numbers from 0 to 20,
r is 0 or 1,
R and R' independently of one another are ethylene, propylene, butylene or an alkylene- or cycloalkylenebismethylene group of the type $-(-C_sH_{2s}-X-)_t C_sH_{2s}-$,
s is from 2 to 8,
t is from 0 to 10, and
X is oxygen or sulfur.

Compounds of this kind are described in more detail in EP 0286887. The (poly)dihydropyridines can be employed in the chlorine-containing polymer expediently in proportions of from 0.001 to 5 parts by weight and, in particular, from 0.005 to 1 part by weight, based on the polymer.

Particular preference is given to thiodiethylenebis[5-methoxycarbonyl-2,6-dimethyl-1,4-dihydropyridine-3-carboxylate].

Alkali metal and alkaline earth metal compounds: By these terms are meant principally the carboxylates of the above-described acids, or also corresponding oxides and hydroxides, carbonates or basic carbonates. Also suitable are mixtures thereof with organic acids. Examples are NaOH, KOH, CaO, $Ca(OH)_2$, MgO, $Mg(OH)_2$, $CaCO_3$, $MgCO_3$, dolomite, huntite, and also Na, K, Ca or Mg salts of fatty acids.

In the case of carboxylates of alkaline earth metals and of Zn, it is also possible to employ adducts thereof with MO or M(OH)$_2$ (M=Ca, Mg, Sr or Zn), so-called overbased compounds.

Preference is given to the use, in addition to the novel stabilizer combination, of alkali metal, alkaline earth metal and/or aluminum carboxylates, for example Na, K, Ca or aluminium stearates. Preferably calcium carboxylates are added.

Perchlorate salts: Examples are those of the formula M(ClO$_4$)$_n$ where M is Li, Na, K, Mg, Ca, Ba, Zn, Al, Ce or La. The index n is, in accordance with the valency of M, 1, 2 or 3. The perchlorate salts can be present as complexes with alcohols or ether alcohols. In this context, the respective perchlorate can be employed in various common forms in which it is supplied; for example as a salt or aqueous solution applied to a carrier material such as PVC, Ca silicate, zeolites or hydrotalcites, or obtained by chemical reaction of hydrotalcite with perchloric acid.

The perchlorates can be employed in an amount of, for example, from 0.001 to 5 parts by weight, expediently from 0.01 to 3 parts by weight and, with particular preference, from 0.01 to 2 parts by weight, based on 100 parts by weight of PVC.

Hydrotalcites and zeolites: The chemical composition of these compounds is known to the skilled worker, for example from the patent documents DE 3843581, U.S. Pat. No. 4000100, EP 062813, WO 93/20135.

Compounds from the series of the hydrotalcites can be described by the general formula III

  (III), in which $M^{2+}$=one or more metals from the group consisting of Mg, Ca, Sr, Zn and Sn, $M^{3+}$=Al or B, $A^y$ is an anion having the valency y, y is a number from 1–2, $0 < x \leq 0.5$, and z is a number from 0–20.

$A^y$ is preferably =OH$^-$, ClO$_4^-$, HCO$_3^-$, CH$_3$COO$^-$, C$_6$H$_5$COO$^-$, CO$_3^{2-}$, SO$_4^{--}$, HSO$_4^-$, $^-$OOC—COO$^-$, (CHOHCOO)$_2^{2-}$, (CH$_2$COO)$_2^{2-}$, CH$_3$CHOHCOO$^-$, HPO$_3^{2-}$ or HPO$_4^{2-}$;

Examples of hydrotalcites are
Al$_2$O$_3$·6MgO·CO$_2$·12H$_2$O, Mg$_{4.5}$Al$_2$·(OH)$_{13}$·CO$_3$·3.5H$_2$O, 4MgO·Al$_2$O$_3$·CO$_2$·9H$_2$O, 4MgO·Al$_2$O$_3$·CO$_2$·6H$_2$O, ZnO·3MgO·Al$_2$O$_3$·CO$_2$·8–9H$_2$ and ZnO·3MgO·Al$_2$O$_3$·CO$_2$·5–6H$_2$O.

Compounds from the series of the zeolites (alkali metal and/or alkaline earth metal aluminosilicates) can be described by the general formula (IV)

  (IV), in which b is the charge of the cation M$^1$;

M$^1$ is an element from the first or second main group, such as Li, Na, K, Mg, Ca, Sr or Ba, or Zn, c:a is a number from 0.8 to 15, preferably from 0.8 to 1.2; and d is a number from 0 to 300, preferably from 0.5 to 30.

Structures can be found, for example, in the "Atlas of Zeolite" by W. M. Meier and D. H. Olson, Butterworth-Heinemann, 3rd ed. 1992.

Examples of zeolites are sodium alumosilicates of the formulae

Na$_{12}$Al$_{12}$Si$_{12}$O$_{48}$·27 H$_2$O [zeolite A], Na$_6$Al$_6$Si$_6$O$_{24}$·2 NaX'. 7.5 H$_2$O, X'=OH, halogen, ClO$_4$ [sodalite]; Na$_6$Al$_6$Si$_{30}$O$_{72}$·24 H$_2$O; Na$_8$Al$_8$Si$_{40}$O$_{96}$·24 H$_2$O; Na$_{16}$Al$_{16}$Si$_{24}$O$_{80}$ ·16 H$_2$O;

Na$_{16}$Al$_{16}$Si$_{32}$O$_{96}$·16 H$_2$O; Na$_{56}$Al$_{56}$Si$_{136}$O$_{384}$·250 H$_2$O [zeolite Y], Na$_{86}$Al$_{86}$Si$_{106}$O$_{384}$·264 H$_2$O [zeolite X];

or the zeolites which can be prepared by partial or complete exchange of the Na atoms by Li, K, Mg, Ca, Sr or Zn atoms, such as (Na,K)$_{10}$ Al$_{10}$Si$_{22}$O$_{64}$·20 H$_2$O; Ca$_{4.5}$Na$_3$[(AlO$_2$)$_{12}$ (SiO$_2$)$_{12}$]·30 H$_2$O;

K$_9$Na$_3$ [(AlO$_2$)$_{12}$ (SiO$_2$)$_{12}$]·27 H$_2$O.

Other suitable zeolites are:

Na$_2$O·Al$_2$O$_3$·(2to 5) SiO$_2$·(3.5 to 10) H$_2$O [zeolite P]

Na$_2$O·Al$_2$O$_3$·2 SiO2·(3.5–10)H$_2$O (zeolite MAP)

or the zeolites which can be prepared by partial or complete exchange of the Na atoms by Li, K or H atoms, such as (Li,Na,K,H)$_{10}$ Al$_{10}$Si$_{22}$O$_{64}$·20 H$_2$O, K$_9$Na$_3$ [(AlO$_2$)$_{12}$ (SiO$_2$)$_{12}$]·27H$_2$O, K$_4$Al$_4$Si$_4$O$_{16}$·6H$_2$O [zeolite K–F], Na$_8$Al$_8$Si$_{40}$O$_{96}$·24 H$_2$O zeolite D, as described in Barrer et al., J. Chem. Soc. 1952, 1561–71, and in U.S. Pat. No. 2,950,952;

Also suitable are the following zeolites:

K offretite, as described in EP-A-400,961; zeolite R, as described in GB 841,812; zeolite LZ-217, as described in U.S. Pat. No. 4,503,023; Ca-free zeolite LZ-218, as described in U.S. Pat. No. 4,333,859; zeolite T, zeolite LZ-220, as described in U.S. Pat. No. 4,503,023; Na$_3$K$_6$Al$_9$Si$_{27}$O$_{72}$·21 H$_2$O [zeolite L]; zeolite LZ-211, as described in U.S. Pat. No. 4,503,023; zeolite LZ-212 as described in U.S. Pat. No. 4,503,023; zeolite O, zeolite LZ-217 as described in U.S. Pat. No. 4,503,023; zeolite LZ-219, as described in U.S. Pat. No. 4,503, 023; zeolite rho, zeolite LZ-214, as described in U.S. Pat. No. 4,503,023;

zeolite ZK-19, as described in Am. Mineral. 54 1607 (1969); zeolite W (K–M), as described in Barrer et al., J. Chem. Soc. 1956, 2882; and Na$_3$Al$_{30}$Si$_{66}$O$_{192}$·98 H$_2$O [zeolite ZK-5, zeolite Q].

Particular preference is given to the use of zeolite P types of the formula M'$_2$O·Al$_2$O$_3$·vSiO$_2$·wH$_2$O (i), in which v is 2 to 5 and w is 3.5 to 10, especially zeolite MAP of the formula i in which v is 2 and w is 3.5 to 10. The substance concerned is, in particular, zeolite Na—P, i.e. M is Na. This zeolite occurs generally in the variants Na—P-1, Na—P-2 and Na—P-3, which differ in their cubic, tetragonal or orthorhombic structure (R. M. Barrer, B. M. Munday, J.Chem.Soc. A 1971, 2909–14). The literature reference just mentioned also describes the preparation of zeolite P-1 and P-2. Zeolite P-3 is accordingly very rare and therefore of virtually no practical interest. The structure of zeolite P-1 corresponds to the gismondite structure known from the abovementioned Atlas of Zeolite Structures. In more recent literature (EP-A-384 070) a distinction is made between cubic (zeolite B or P$_c$) and tetragonal (zeolite P$_1$) zeolite of the P type. Also mentioned therein are more recent zeolites of the P type with Si:Al ratios below 1.07:1. These are zeolites bearing the designation MAP or MA—P, for Maximum Aluminium P. Depending on the preparation process, zeolite P may include small fractions of other zeolites. Highly pure zeolite P has been described in WO 94/26662.

In the context of the invention it is also possible to use those finely divided, water-insoluble sodium alumosilicates which have been precipitated in the presence of watersoluble inorganic or organic dispersants and crystallized. These can be introduced in the reaction mixture in any desired manner, prior to or during the precipitation or crystallization.

Preference is given to Na-zeolite A and Na-zeolite P.

The hydrotalcites and zeolites can be naturally occurring minerals or synthetically prepared compounds.

The hydrotalcites and/or zeolites can be employed in amounts of, for example from 0.1 to 50 parts by weight, expediently from 0.1 to 10 parts by weight and, in particular, from 0.1 to 5 parts by weight, based on 100 parts by weight of halogen-containing polymer.

Alkali metal alumocarbonates (dawsonites): These compounds can be represented with the formula V $$\{(M^2{}_2O)_f.(Al_2O_3)_g.Z^1{}_o.hH_2O\} \tag{V},$$

in which $M^2$ is H, Li, Na, K, $Mg_{1/2}$, $Ca_{1/2}$, $Sr_{1/2}$ or $Zn_{1/2}$; $Z^1$ is $CO_2$, $SO_2$, $(Cl_2O_7)_{1/2}$, $B_4O_6$, $S_2O_2$ (thiosulfate) or $C_2O_2$ (oxalate); f, if $M^2$ is $Mg_{1/2}$ or $Ca_{1/2}$, is a number between 1 and 2, in all other cases a number between 1 and 3; g is a number between 1 and 4; o is a number between 2 and 4; and h is a number between 0 and 30.

The alumo salt compounds of the formula (V) which can be used can be naturally occurring minerals or synthetically prepared compounds. The metals can be partially substituted by one another. The abovementioned alumo salt compounds are crystalline, partially crystalline or amorphous or can be present in the form of a dried gel. The alumo salt compounds can also be present in rarer, crystalline modifications. A process for preparing such compounds is specified in EP 394670. Examples of naturally occurring alumo salt compounds are indigirite, tunisite, alumohydrocalcite, para-alumohydrocalcite, strontiodresserite and hydrostrontio-dresserite. Further examples of alumo salt compounds are potassium alumocarbonate $\{(K_2O).(Al_2O_3).(CO_2)_2.2H_2O\}$, sodium alumothiosulfate $\{(Na_2O).(Al_2O_3).(S_2O_2)_2.2H_2O\}$, potassium alumosulfite $\{(K_2O).(Al_2O_3).(SO_2)_2.2H_2O\}$, calcium alumooxalate $\{(CaO).(Al_2O_3).(C_2O_2)_2.5H_2O\}$, magnesium alumotetraborate $\{(MgO).(Al_2O_3).(B_4O_6)_2.5H_2O\}$, $\{([Mg_{0.2}Na_{0.6}]_2O).(Al_2O_3).(CO_2)_2.4.1H_2O\}$, $\{([Mg_{0.2}Na_{0.6}]_2O).(Al_2O_3).(CO_2)_2.4.3H_2O\}$ and $\{([Mg_{0.3}Na_{0.4}]_2O).(Al_2O_3).(CO_2)_{2.2}.4.9H_2O\}$.

The mixed alumo salt compounds can be obtained in accordance with methods known per se by cationic exchange, preferably from the alkali metal alumo salt compounds, or by combined precipitation (see for example U.S. Pat. No. 5,055,284).

Preferred alumo salt compounds are those of the above formula V in which $M^2$ is Na or K; $Z^1$ is $CO_2$, $SO_2$ or $(Cl_2O_7)_{1/2}$; f is 1–3; g is 1–4; o is 0–20. $Z^1$ is particularly preferably $CO_2$.

Also preferred are compounds which can be represented by the following formulae:

$M^2{}_2O.Al_2O_3.(CO_2)_2.hH_2O$ (Va), $(M^2{}_2O)_2.(Al_2O_3)_2.(CO_2)_2.hH_2O$ (Vb), $M^2{}_2O.(Al_2O_3)_2.(CO_2)_2.hH_2O$ (Vc) in which $M^2$ is a metal such as Na, K, $Mg_{1/2}$, $Ca_{1/2}$, $Sr_{1/2}$ or $Zn_{1/2}$ and h is a number from 0 to 12.

Particular preference is given to sodium alumodihydroxy-carbonate (DASC) and the homologous potassium compound (DAPC).

The dawsonites can be employed in an amount of, for example, from 0.01 to 50 parts by weight, expediently from 0.1 to 10 parts by weight, particularly preferably from 0.1 to 5 parts by weight, based on 100 parts by weight of halogen-containing polymer.

The novel stabilizer combination can be used together with further additives which are customary for the processing and stabilizing of chlorine-containing polymers, examples being:

antioxidants: Suitable examples are:

1. Alkylated monophenols, for example 2,6-di-tert-butyl-4-methylphenol, 2-butyl4,6-dimethylphenol, 2,6-di-tert-butyl-4-ethylphenol, 2,6-di-tert-butyl-4-n-butylphenol, 2,6-ditert-butyl-4-isobutylphenol, 2,6-dicyclopentyl-4-methylphenol, 2-(α-methylcyclohexyl)4,6-dimethylphenol, 2,6-dioctadecyl-4-methylphenol, 2,4,6-tricyclohexylphenol, 2,6-di-tertbutyl-4-methoxymethylphenol, 2,6-dinonyl-4-methylphenol, 2,4-dimethyl-6-(1'-methylundec-1'-yl)-phenol, 2,4-dimethyl-6-(1'-methylheptadec-1'-yl)phenol, 2,4-dimethyl-6-(1'-methyl tridec-1'-yl)phenol and mixtures thereof.

2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

3. Hydroquinones and alkylated hydroquinones, for example 2,6-di-tert-butyl4-methoxyphenol, 2,5-di-tert-butylhydroquinone, 2,5-di-tert-amylhydroquinone, 2,6-diphenyl4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

4. Tocopherols, for example α-tocopherol, β-tocopherol, γ-tocopherol, δ-tocopherol and mixtures thereof (vitamin E).

5. Hydroxylated thiodiphenyl ethers, for example 2,2'-thiobis(6-tert-butyl-4-methyl-phenol), 2,2'-thiobis(4-octylphenol), 4,4'-thiobis(6-tert-butyl-3-methylphenol), 4,4'-thiobis-(6-tert-butyl-2-methylphenol), 4,4'-thiobis(3,6-di-sec-amylphenol), 4,4'-bis(2,6-dimethyl-4-hydroxyphenyl) disulfide.

6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis-(6-nonyl-4-methylphenol), 2,2'-methylenebis(4,6-di-tert-butylphenol), 2,2'-ethylidenebis-(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl) dicyclopentadiene, bis[2-(3'-tert-butyl-2'-hydroxy-5'-methylbenzyl)-6-tert-butyl4-methylphenyl]terephthalate, 1,1-bis(3,5-dimethyl-2-hydroxyphenyl)butane, 2,2-bis(3,5-ditert-butyl-4-hydroxyphenyl) propane2,2-bis(5-tert-butyl-4-hydroxy-2-methylphenyl)-4-ndodecylmercaptobutane, 1,1,5,5-tetra-(5-tert-butyl-4-hydroxy-2-methylphenyl) pentane.

7. O-, N- and S-benzyl compounds, for example 3,5,3', 5'-tetra-tert-butyl-4,4'-dihydroxydibenzyl ether, octadecyl 4-hydroxy-3,5-dimethylbenzylmercaptoacetate, tris(3,5-ditert-butyl-4-hydroxybenzyl)amine, bis(4-tert-butyl-3-hydroxy-2,6-dimethylbenzyl)dithio-terephthalate, terephthalate, bis(3,5-di-tert-butyl-4-hydroxybenzyl) sulfide, isooctyl 3,5-di-tert-butyl4-hydroxybenzylmercaptoacetate.

8. Hydroxybenzylated malonates, for example dioctadecyl 2,2-bis(3,5-di-tert-butyl2-hydroxybenzyl) malonate, dioctadecyl 2-(3-tert-butyl-4-hydroxy-5-methylbenzyl) malonate, didodecyl mercaptoethyl-2,2-bis(3,5-di-tert-butyl-4-hydroxybenzyl)malonate, di-[4-(1,1,3,3-tetramethylbuthyl) phenyl]2,2-bis(3,5-di-tert-butyl-4-hydroxybenzyl)malonate.

9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tertbutyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

12. Acylaminophenols, for example 4-hydroxylauranilide, 4-hydroxystearanilide, octyl N-(3,5-di-tert-butyl-4-hydroxyphenyl)carbamate.

13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

14. Esters of β-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonane-diol, ethylene glycol, 1,2-propanediol, neopentyl glycol, thiodiethylene glycol, diethylene glycol, triethylene glycol, pentaerythritol, tris(hydroxyethyl) isocyanurate, N,N'bis(hydroxy-ethyl)oxalamide, 3-thiaundecanol, 3-thiapentadecanol, trimethylhexanediol, trimethylol-propane, 4-hydroxymethyl-1-phospha-2,6,7-trioxabicyclo[2.2.2]octane.

15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

16. Esters of 3.5-di-tert-butyl-4-hydroxvphenvl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

17. Amides of β-(3.5-di-tert-butyl-4-hydroxyphenyl) propionic acid, for example N,N'-bis (3,5di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine. If desired it is also possible to employ a mixture of antioxidants differing in structure.

The antioxidants can be employed in an amount of, for example, from 0.01 to 10 parts by weight, expediently from 0.05 to 10 parts by weight and, in particular, from 0.05 to 5 parts by weight, based on 100 parts by weight of PVC.

UV absorbers and light stabilizers: examples of these are:

1. 2-(2'-Hydroxyphenyl)benzotriazoles, for example 2-(2'-hydroxy-5'-methylphenyl)-benzotriazole, 2-(3', 5'-di-tert-butyl-2'-hydroxyphenyl)benzotriazole, 2-(5'-tert-butyl-2'-hydroxy-phenyl) benzotriazole, 2-(2'-hydroxy-5'-(1 1,3,3-tetramethylbutyl)phenyl)benzotriazole, 2-(3', 5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'hydroxyphenyl)-benzotriazole, 2-(2'-hydroxy-4'-octoxyphenyl) benzotriazole, 2-(3', 5'-di-tert-amyl-2'-hydroxy-phenyl) benzotriazole, 2-(3', 5'-bis(α,α-dimethylbenzyl)-2'-hydroxyphenyl)-benzotriazole, a mixture of 2-(3'-tert-butyl-2'-hydroxy-5'-(2-octyloxycarbonylethyl)phenyl)-5chlorobenzo-triazole 2-(3'-tert-butyl-5'-[2-(2-ethylhexyloxy)carbonylethyl]-2'-hydroxyphenyl)-5-chloro-benzotriazole, 2-(3'-tert-butyl-2'-hydroxy-5'-(2-methoxycarbonylethyl) phenyl)-5chlorobenzo-triazole, 2-(3'-tert-butyl-2'-hydroxy-5'-(2methoxycarbonylethyl) phenyl)benzotriazole, 2-(3'-tert-butyl-2'-hydroxy-5'-(2octyloxycarbonylethyl)phenyl)benzotriazole, 2-(3'-tert-butyl-5'-[2-(2ethylhexyloxy)carbonylethyl]-2'-hydroxyphenyl)benzotriazole, 2-(3'-dodecyl-2'-hydroxy-5'methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriaz with polyethylene glycol 300;

where R"=3'-tert-butyl-4'-hydroxy-5'-2H-benzotriazol-2-ylphenyl.

2. 2-Hydroxybenzophenones, for example the 4-hydroxy, 4-methoxy, 4-octoxy, 4-decyloxy, 4-dodecyloxy, 4-benzyloxy, 4,2', 4'-trihydroxy and 2'-hydroxy-4,4'-dimethoxy derivative.

3. Esters of substituted or unsubstituted benzoic acids, for example 4-tert-butyl-phenyl salicylate, phenyl salicylate, octylphenyl salicylate, dibenzoylresorcinol, bis(4-tertbutylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl α-cyano-β,β-diphenylacrylate or isooctyl α-cyano-β, β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, such as of 2-hydroxy-4-methylphenyl undecyl ketoxime, nickel complexes of 1-phenyl-4-lauroyl5-hydroxypyrazole, with or without additional ligands.

6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl 3,5-di-tert-butyl-4-hydroxybenzylmalonate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediIyl)-bis (3,3,5,5-tetramethylpiperazinone), 4-benzoyl-2,2,6,6-tetramethylpiperidine, 4-stearyloxy-2,2,6,6-tetramethylpiperazinone), bis(1 ,2,2,6,6-pentamethylpiperidyl)-2-n-butyl-2-(2-hydroxy3,5-di-tert-butylbenzyl) malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis (2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triaziine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(2,2,6,6-tetramethyl4-piperidyl)pyrrolidine-2,5-dione.

7. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'ethyloxanilide, N,N'-bis(3-dimethylaminopropyl)oxalamide, 2-ethoxy-5-tert-butyl-2'ethyloxanilide and its mixture with 2-ethoxy-2'-ethyl-5,4'-di-tert-butyloxanilide and mixtures of o- and p-methoxy and of o- and p-ethoxy-disubstituted oxanilides.

8. 2-(2-Hydroxyphenyl)-1,3,5-triazines, for example 2,4, 6-tris(2-hydroxy-4-octyloxy-phenyl)-1,3,5-triazine, 2-(2-hydroxy-4-octyloxyphenyl)-4,6-bis(2,4-dimethylphenyl)-,3,5-triazine, 2-(2,4-dihydroxyphenyl)-4,6-bis(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyl-oxyphenyl)-4,6-bis(4-methylphenyl)-1,3,5-triazine, 2-(2-hydroxy-4-dodecyloxyphenyl)-4,6-bis-(2,4-dimethylphenyl)-1,3,5-triazine, 2-[2-hydroxy-4-(2-hydroxy-3-butyloxypropyloxy)phenyl]-4,6-bis (2,4-dimethylphenyl)-1,3,5-triazine, 2-[2-hydroxy-4-(2-hydroxy-3-octyloxypropoxy)-phenyl]-4,6-bis(2,4-dimethylphenyl)-1,3,5-triazine. The novel stabilizer mixture is preferred with alkali metal or alkaline earth metal carboxylates, especially calcium carboxylates, with aluminium carboxylates, with 1,3-dicarbonyl compounds, with dihydropyridines, with phosphites or with combinations of these substances.

Plasticizers: Examples of suitable organic plasticizers are those from the following groups: A) Phthalic esters:

Examples of such plasticizers are dimethyl, diethyl, dibutyl, dihexyl, di-2-ethylhexyl, di-n-octyl, di-isooctyl, di-isononyl, di-isodecyl, di-isotridecyl, dicyclohexyl, di-methylcyclohexyl, dimethylglycol, dibutylglycol, benzyl butyl and diphenyl phthalate, and also mixtures of phthalates, such as $C_{7-9}$- and $C_{9-11}$alkyl phthalates from predominantly linear alcohols, $C_{6-10}$-n-alkyl phthalates and $C_{8-10}$-n-alkyl phthalates. Among these, preference is given to dibutyl, dihexyl, di-2-ethylhexyl, di-n-octyl, di-isooctyl, di-isononyl, di-isodecyl, di-isotridecyl and benzyl butyl phthalate and to the abovementioned mixtures of alkyl phthalates. Particular preference is given to di-2-ethylhexyl, di-isononyl and di-isodecyl phthalate, which are also known under the common abbreviations DOP (dioctyl phthalate, di-2-ethylhexyl phthalate), DINP (diisononyl phthalate), and DIDP (diisodecyl phthalate).

B) Esters of aliphatic dicarboxylic acids, especially esters of adipic, azeleic and sebacic acid Examples of such plasticizers are di-2-ethylhexyl adipate, di-isooctyl adipate (mixture), di-isononyl adipate (mixture), di-isodecyl adipate (mixture), benzyl butyl adipate, benzyl octyl adipate, di-2-ethylhexyl azelate, di-2-ethylhexyl sebacate and di-isodecyl sebacate (mixture). Preference is given to di-2-ethylhexyl adipate and di-isooctyl adipate.

C) Trimellitic esters, for example tri-2-ethylhexyl trimellitate, tri-isodecyl trimellitate (mixture), tri-isotridecyl trimellitate, tri-isooctyl trimellitate (mixture) and also tri-$C_{6-8}$alkyl, tri-$C_{6-10}$alkyl, tri-$C_{7-9}$alkyl and tri-$C_{9-11}$alkyl trimellitates. The latter trimellitates are formed by esterification of trimellitic acid with the corresponding mixtures of alcanols. Preferred trimellitates are tri-2-ethylhexyl trimellitate and the abovementioned trimellitates from alcanol mixtures. Common abbreviations are TOTM (trioctyl trimellitate, tri-2-ethylhexyl trimellitate), TIDTM (triisodecyl trimellitate) and TITDTM (triisotridecyl trimellitate).

D) Epoxy plasticizers

These are principally epoxidized unsaturated fatty acids such as epoxidized soybean oil.

E) Polymer plasticizers

The most common starting materials for the preparation of the polyester plasticizers are: dicarboxylic acids such as adipic, phthalic, azeleic and sebacic acid; and diols such as 1,2-propanediol, 1,3-butanediol, 1,4-butanediol, 1,6-hexanediol, neopentylglycol and diethylene glycol.

F) Phosphoric esters

Examples of such phosphoric esters are tributyl phosphate, tri-2-ethylbutyl phosphate, tri-2ethylhexyl phosphate, trichloroethyl phosphate, 2-ethylhexyl diphenyl phosphate, cresyl diphenyl phosphate, triphenyl phosphate, tricresyl phosphate and trixylenyl phosphate. Preference is given to tri-2-ethylhexyl phosphate and to ®Reofos 50 and 95 (from FMC).

G) Chlorinated hydrocarbons (paraffin)

H) Hydrocarbons i) Monoesters, for example butyl oleate, phenoxyethyl oleate, tetrahydrofurfuryl oleate and alkylsulfonic esters.

J) Glycol esters, for example diglycol benzoates.

Definitions and examples of plasticizers from groups A) to J) can be found in the following handbooks:

"Taschenbuch der Kunststoffadditive", eds. R. Gachter and H. Muller, Carl Hanser Verlag, 1989, Chapter 5, pp. 341–442.

"PVC Technology", ed. W.V. Titow, 4th. Ed., Elsevier Publishers, 1984, Chapter 6, pages 147–180.

It is also possible to employ mixtures of different plasticizers.

The plasticizers can be employed in an amount of, for example, from 5 to 120 parts by weight, expediently from 10 to 100 parts by weight, based on 100 parts by weight of PVC.

Examples of suitable lubricants are: montan wax, fatty acid esters, PE waxes, amide waxes, chlorinated paraffins, glycerol esters or alkaline earth metals soaps, and silicone-based lubricants as described in EP 225261. Lubricants which can be used are also described in "Taschenbuch der Kunststoffadditive", eds. R. Gachter and H. Muller, Carl Hanser Verlag, 3rd edition, 1989, pages 478–488.

Fillers: Examples of possible fillers ("Handbook of PVC-Formulating" by E. J. Wickson, John Wiley & Sons, New York 1993, pp. 393–449) and reinforcing agents ("Taschenbuch der Kunststoffadditive", eds. R. Gachter and H. Muller, Carl Hanser Verlag, 3rd edition, 1989, pages 549–615) are: calcium carbonate, dolomite, wollastonite, magnesium oxide, magnesium hydroxide, silicates, glass fibres, talc, kaolin, chalk, mica, metal oxides and metal hydroxides, carbon black or graphite), preference being given to chalk.

Pigments: Suitable substances are known to the skilled worker. Examples of inorganic pigments are $TiO_2$, carbon black, $Fe_2O_3$, $Sb_2O_3$, $(Ti,Ba,Sb)O_2$, $Cr_2O_3$, spinels such blue and cobalt green, Cd(S,Se), ultramarine blue. Preference is given to $TiO_2$, including its micronized form. Examples of organic pigments are azo pigments, phthalocyanine pigments, quinacridone pigments, perylene pigments, pyrrolopyrrole pigments and anthraquinone pigments. Further details are to be found in "Handbook of PVC Formulating", E. J. Wickson, John Wiley & Sons, New York 1993, pp. 449–474.

Examples of the chlorine-containing polymers to be stabilized or their recyclates are: polymers of vinyl chloride, vinyl resins containing vinyl chloride units in their structure, such as copolymers of vinyl chloride and vinyl esters of aliphatic acids, especially vinyl acetate, copolymers of vinyl chloride with esters of acrylic and methyacrylic acid and with acrylonitrile, copolymers of vinyl chloride with diene compounds and unsaturated dicarboxylic acids or their anhydrides, such as copolymers of vinyl chloride with diethyl maleate, diethyl fumarate or maleic anhydride, post-chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and copolymers thereof with vinyl chloride and other polymerizable compounds; polymers of vinyl chloroacetate and dichlorodivinyl ether; chlorinated polymers of vinyl acetate, chlorinated polymeric esters of acrylic acid and of alpha-substituted acrylic acid; polymers of chlorinated styrenes, for example dichlorostyrene; chlorinated rubbers; chlorinated polymers of ethylene; polymers and post-chlorinated polymers of chlorobutadiene and copolymers thereof with vinyl chloride, chlorinated natural and synthetic rubbers; and mixtures of the abovementioned polymers with each other or with other polymerizable compounds.

In the context of this invention the term PVC also includes copolymers or graft polymers of PVC with polymerizable compounds such as acrylonitrile, vinyl acetate or ABS, which can be suspension, bulk or emulsion polymers. Preference is given to PVC homopolymer, alone or in combination with polyacrylates.

Also included are the graft polymers of PVC with EVA, ABS and MBS. Other preferred substrates are mixtures of the abovementioned homo- and copolymers, especially, vinyl chloride homopolymers, with other thermoplastic and/or elastomeric polymers, especially blends with ABS, MBS, NBR, SAN, EVA, CPE, MBAS, PMA, PMMA, EPDM and polylactones.

Preference is given to suspension polymers and bulk polymers, and to emulsion polymers.

A particularly preferred chlorine-containing polymer is polyvinyl chloride, especially as suspension polymer and bulk polymer.

For stabilization in the context of this invention, further suitable polymers are, in particular, recyclates of chlorine-containing polymers, these polymers being the polymers described in more detail above that have undergone damage through processing, use or storage. PVC recyclate is particularly preferred. The recyclates may also include small amounts of extraneous substances, for example paper, pigments, adhesives, which are often difficult to remove. These extraneous substances may also arise from contact with various materials in the course of use or of reprocessing, examples being residues of fuel, fractions of coating material, traces of metal and residues of initiator.

The stabilizer mixture is employed in a manner familiar to the skilled worker. The stabilizer mixture can also, for example, be subjected to shaping together with conventional additives prior to the actual use, in order to give, for example, granules or extrudate or a paste.

The present invention additionally provides for the use of the stabilizer mixture just described—as it is or in the form of granules, extrudate or paste and also in conjunction with lubricants (so-called one-pack)—for stabilizing a halogen-containing polymer or polymer recyclate, as well as a process for stabilizing chlorine-containing polymers, which comprises adding thereto a stabilizer combination as described above. For the individual stabilizers and for the halogen-containing polymer itself, the preferences expressed above apply; similarly, it is possible in addition for one of the above-described further constituents to be used.

The stabilizer mixture can be added to the polymer in a known manner, in which case the abovementioned stabilizers and, if desired, further additives can be mixed with the halogen—containing polymer using known devices such as mixers, compounders, extruders, mills and the like. In this context, the stabilizers can be added individually or in a mixture or else in the form of a masterbatch. The invention therefore also provides a process for stabilizing halogen-containing polymer which comprises mixing the stabilizer components and, if desired, further additives with the PVC using devices such as calenders, mixers, compounders, extruders and the like. The invention also provides the polymer compositions stabilized in this way comprising the novel stabilizer mixture. They can be brought into the desired form by known methods. Examples of such methods are calendering, extrusion, injection moulding, sintering or spinning, and also extrusion blow moulding or processing by the plastisol process. The polymer compositions can also be processed to foams.

The invention also provides for the use of the stabilized polymer compositions for producing mouldings which can be produced from halogen-containing polymer. The novel polymer compositions are suitable for semirigid and flexible formulations, for instance for flexible formulations for wire sheathing and cable insulation applications. In the form of semirigid formulations, the novel polymer compositions are suitable for decorative films, foams, agricultural films, hoses, sealing profiles, office films, extruded profiles and panels, flooring sheets and panels, coated products and synthetic leather, and also crash pad sheets (for use in the automotive sector). In the form of rigid formulations, the novel polymer compositions are suitable for hollow articles (bottles), packaging films (thermoform films), blown films, crash pad sheets (cars), pipes, foams, heavy profiles (window frames), transparent wall profiles, construction profiles, sidings, fittings and apparatus enclosures (computers, domestic appliances) and also other injection-moulded articles. Examples of the use of the polymer compositions, stabilized in accordance with the invention, as plastisol are synthetic leather, floorings, textile coatings, wallpapers, coil coatings and underbody protection for motor vehicles. Examples of sinter applications of the polymer compositions stabilized in accordance with the invention are slush, slush mould and coil coatings.

The preparation of N-piperidinyltriazines is known from the literature (cf. e.g. Houben-Weyl "Methoden der organischen Chemie" vol. VIII, pp. 233–237, SAUERSTOFF-VERBINDUNGEN III, Thieme Verlag Stuttgart 1952). Starting materials which can be employed for the reaction with various N-piperidinylamines are cyanuric chloride, diaminochloro-1,3,5-triazine or variously substituted bisdialkylaminochloro-1,3,5-triazines or dialkylamino- and/or alkylamino-dichloro-1,3,5-triazines. The Examples which follow illustrate the invention in more detail but without restricting it. As in the remainder of the description, parts and percentages are by weight unless stated otherwise.

Example 1: N-[2.2.6,6-Tetramethylpiperidine-4-yl] melamine. 246.2 g (1.575 mol) of 4-amino-2,2,6,6-tetramethylpiperidine are dissolved in 2l of water, and the suspension obtained after adding 218.4 g (1.50 mol) of diaminochloro-1,3,5-triazine (DACT) is heated to 95°–98° C. with vigorous stirring. Then, over the course of about 2 h, a solution of 60 g NaOH in 500 ml of water is added dropwise. The slightly opalescent solution is stirred at about 100° C. for 2 h more. After clarifying filtration with the addition of a filter aid (PRIMISIL®), the solution is concentrated under reduced pressure to about 50% of the original volume. The precipitated crystals are filtered off with suction, washed free of chloride with ice-water and dried under reduced pressure at 140° C.

Yield: 302 g (76% of theory)

Melting point: 210°–215° C.

Elemental analysis: found (calc.)

C: 54.32 (53.96), H 8.74 (8.92), N 36.95 (36.23)

The following compounds are prepared by a procedure similar to that of Example 1, in some cases working in an anhydrous medium, in nonpolar solvents, in the presence of a tertiary base and/or solid NaOH.

Example 2:

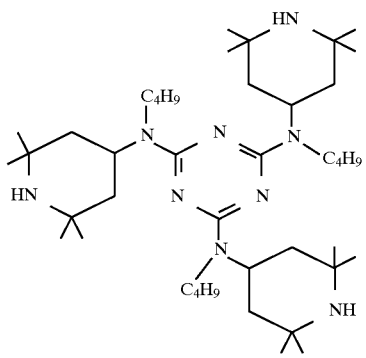

m.p: 165°–166° C.

Example 3:

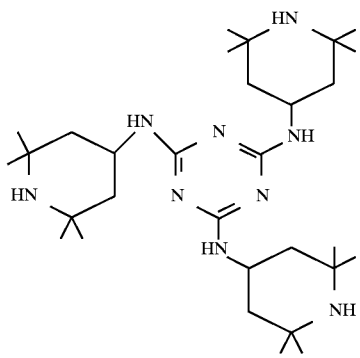

m.p: 217°–19° C.

Example 4:

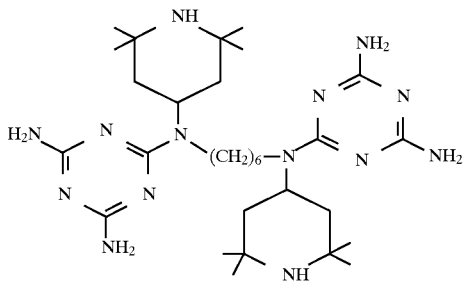

m.p: 145° C.

Example 5

To prepare the stabilizers I and II, a Zn/Ca-stearate mixture is mixed intensely in a tumble mixer with a commercially available 1,3-diketone (Stab. I) and, further, with the respective piperidinylmelamine compound in a ratio of 8:2:1.5 (Stab. II, III) for a period of 1.5 hours. In each case 1.0 part (Stab. I) or 1.15 parts (Stab. II, III) of these stabilizer mixtures are mixed with 100 parts of S-PVC (K value 70) and 21 parts of a mixture of dioctyl phthalate/epoxidized soya oil and a commercially available liquid aryl-alkyl phosphite, and the mixtures are plasticated on mixing rolls at 190° C. for 5 minutes. Test specimens are cut from the resulting film (thickness 0.2 mm) and are subjected to thermal stress in a Mathis Thermotakter at 180° C. for the period indicated in Table 2 below. Subsequently, the yellowness index (YI) is determined in accordance with ASTM-1925–70. The lower the YI found, the more effective the prevention by the stabilizer system of yellowing and therefore damage of the material. The long-term thermal stability of the stabilized polymer is evident from the sudden onset of massive discoloration. A stabilizer is all the more effective the longer this discoloration under thermal stress is delayed.

TABLE 2

| Stabilizer of Ex. | Heat test: YI of the test specimens at 180° C. | | | | | Interrupted at time [min] |
|---|---|---|---|---|---|---|
| | Test duration [min] | | | | | |
| | 0 | 6 | 12 | 24 | 48 | |
| I | — | 3.3 | 4.1 | 5.0 | black | 14 |
| II | 1 | 3.7 | 4.2 | 4.7 | 6.7 24.3 | 59 |
| III | 3 | 3.9 | 4.4 | 4.8 | 6.7 13.5 | 71 |

What is claimed is:

1. A stabilizer combination comprising organozinc compounds and compounds of the formula I

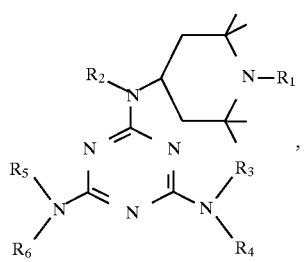
(I)

$R_1$ is H, $C_{1-8}$alkyl-, $C_{3-8}$alkenyl-, $C_{5-8}$cycloalkyl- or $C_{7-9}$phenylalkyl-;

$R_2$ is H, $C_{1-8}$alkyl-, $C_{3-8}$alkenyl-, $C_{5-8}$cycloalkyl-, HO—$C_2H_4$—, HO—$C_3H_6$—, $(C_{1-4}$alkyl$)_2$N—$(CH_2)_k$—

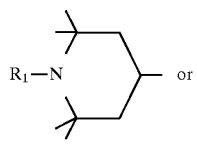

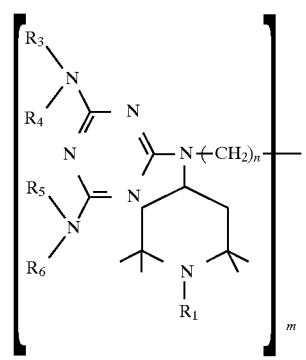

$R_3$, $R_4$, $R_5$, and $R_6$ independently of one another are H, $C_{1-8}$alkyl-, $C_{5-8}$cycloalkyl-, $C_{1-9}$phenylalkyl-, $C_{3-8}$alkenyl-, HO—$C_2H_4$—, HO—$C_3H_6$—, $(C_{1-4}$alkyl$)_2$N—$(CH_2)_k$—, phenyl or phenyl substituted by HO—, $H_2$N—, $C_{1-4}$alkyl- or -alkoxy-, or $R_3$, $R_4$, $R_5$, and $R_6$ are

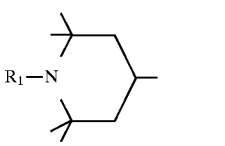

and $R_3$ and $R_4$ and/or $R_5$ and $R_6$ can alternatively be attached to one another via methylene groups, which are adjacent or separated by O, S, or $C_{1-4}$alkyl-N atoms; and n is 2 to 12;

k is 2 to 6; and m is 0 or 1.

2. A stabilizer combination according to claim 1, in which $R_1$ H or $C_{1-8}$alkyl-;

$R_2$ is H, $C_{1-8}$alkyl-, HO—$C_2H_4$—, HO—$C_3H_6$—, $(C_{1-4}$alkyl$)_2$N—$(CH_2)_k$—,

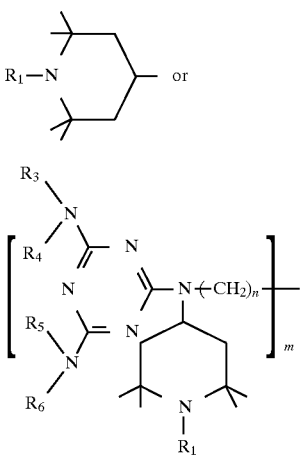

$R_3$, $R_4$, $R_5$, $R_6$ are H, $C_{1-8}$alkyl-, HO—$C_2H_4$—, HO—$C_3H_6$—, $(C_{1-4}$alkyl$)_2$N—$(CH_2)_k$—,

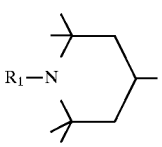

or $NR_3R_4$ and/or $NR_5R_6$ are groups of the formulae

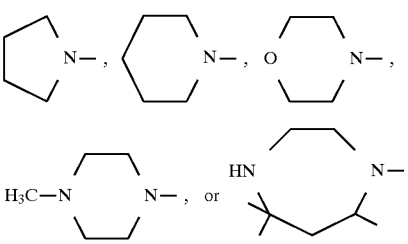

3. A stabilizer combination according to claim 2, in which $R_1$ is H or $C_{1-4}$alkyl-;

$R_2$ is H, $C_{1-4}$alkyl-, $(C_{1-4}alkyl)_2N\text{—}(CH_2)_k\text{—}$,

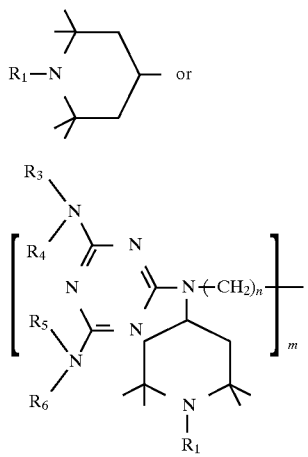

or $R_3, R_4, R_5, R_6$ are H, $C_{1-4}$alkyl-, $(C_{1-4}alkyl)_2N\text{—}(CH_2)_k\text{—}$,

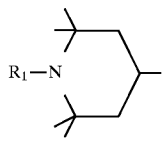

or $NR_3R_4$ and/or
$NR_5R_6$ are groups of the formulae

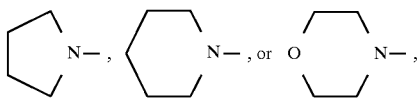

and n is 2 to 6;
k is 2 or 3; and
m is 0 or 1.

4. A stabilizer combination according to claim 3, in which $R_3, R_4, R_5, R_6$ are H,

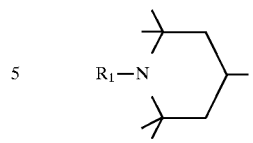

or $NR_3R_4$ and/or $NR_5R_6$ are groups of the formula

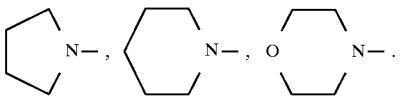

5. A stabilizer combination according to claim 1, which additionally comprises alkali- metal carboxylates and/or alkaline earth metal carboxylates.

6. A stabilizer combination according to claim 1, which additionally comprises calcium carboxylates.

7. A stabilizer combination according to claim 1, which additionally comprises aluminium carboxylates or aluminium enolates.

8. A stabilizer combination according to claim 1, which additionally comprises at least one further substance from the groups consisting of epoxides and epoxidized fatty acid esters, phosphites, thiophosphites and thiophosphates, polyols, 1,3-dicarbonyl compounds, mercaptocarboxylic esters, dihydropyridines, antioxidants, light stabilizers and UV absorbers, alkali metal compounds and alkaline earth metal compounds, perchlorate salts, zeolites, hydrotalcites and dawsonites.

9. A composition comprising a chlorine-containing polymer and a stabilizer mixture according to claim 1.

10. A process for stabilizing chlorine-containing polymers, which comprises adding thereto a stabilizer combination according to claim 1.

11. A compound of the formula 1, as described in claim 1, wherein at least one of the radicals $R_2$–$R_6$ is $(C_{1-4}alkyl)_2 N\text{—}(CH_2)_k\text{—}$.

12. A compound of the formula 1, as described in claim 1, wherein $R_3$–$R_6$ are hydrogen and the remaining radicals are as defined therein.

* * * * *